United States Patent [19]

Conero et al.

[11] Patent Number: 4,680,977
[45] Date of Patent: Jul. 21, 1987

[54] OPTICAL FLOW SENSOR

[75] Inventors: Ronald S. Conero; Terry L. Landis, both of San Diego, Calif.

[73] Assignee: Ivac Corporation, San Diego, Calif.

[21] Appl. No.: 708,969

[22] Filed: Mar. 6, 1985

[51] Int. Cl.[4] .......................... G01F 13/00; A61M 5/14
[52] U.S. Cl. ................................ 73/861.41; 356/338; 604/253
[58] Field of Search .................. 73/861.41, 861.05; 128/DIG. 13; 604/251, 253, 65; 250/574, 573, 576; 356/440, 442, 335, 336, 338

[56] References Cited

U.S. PATENT DOCUMENTS

| 2,333,791 | 11/1943 | Hutchinson, Jr. | 73/861.41 |
| 2,866,379 | 12/1958 | Viet | 250/573 |
| 2,873,644 | 2/1959 | Kremen et al. | 250/574 |
| 2,967,450 | 1/1961 | Shields | 73/861.41 |
| 3,199,346 | 8/1965 | Stewart | 73/861.05 |
| 3,279,305 | 10/1966 | Muta et al. | 356/442 |
| 3,596,515 | 8/1971 | Cramer . | |
| 3,826,577 | 7/1974 | Irwin | 356/438 |
| 3,884,228 | 5/1975 | Hahn . | |
| 4,018,362 | 4/1977 | Ubaud . | |
| 4,038,981 | 4/1977 | LeFevre et al. . | |
| 4,038,982 | 8/1977 | Burke et al. . | |
| 4,095,904 | 6/1978 | Klein et al. | 250/576 |
| 4,173,224 | 11/1979 | Marx et al. . | |
| 4,181,130 | 1/1980 | Bailey . | |
| 4,314,484 | 2/1982 | Bowman . | |
| 4,383,252 | 5/1983 | Purcell et al. . | |
| 4,397,642 | 8/1983 | Lamadrid . | |
| 4,397,648 | 8/1983 | Knute . | |

FOREIGN PATENT DOCUMENTS

| 0112699 | 7/1984 | European Pat. Off. . | |
| WO82/00591 | 3/1982 | PCT Int'l Appl. | 128/DIG. 13 |
| 1437738 | 6/1973 | United Kingdom . | |

Primary Examiner—Herbert Goldstein
Attorney, Agent, or Firm—Fulwider Patton Rieber Lee & Utecht

[57] ABSTRACT

An improved optical flow sensor for optically detecting and measuring the flow of a fluid through a drip chamber assembly. The sensor comprises an optical energy-emitting chip sealed within a first lens block having a refracting lens in one surface and an optical energy detecting chip sealed within a second lens block having a refracting lens in one surface. The two lens blocks are positioned on the two parallel arms of a "U"-shaped base with their lens surfaces facing each other across the open space between the arms of the "U". The drip chamber assembly has transparent walls defining a drip chamber, and the lenses compensate for the refractive effects of the walls of the drip chamber assembly on the optical energy passing through. As drops of fluid fall through the chamber, they intersect the optical energy passing through the chamber and produce a corresponding output signal from the detector.

21 Claims, 7 Drawing Figures

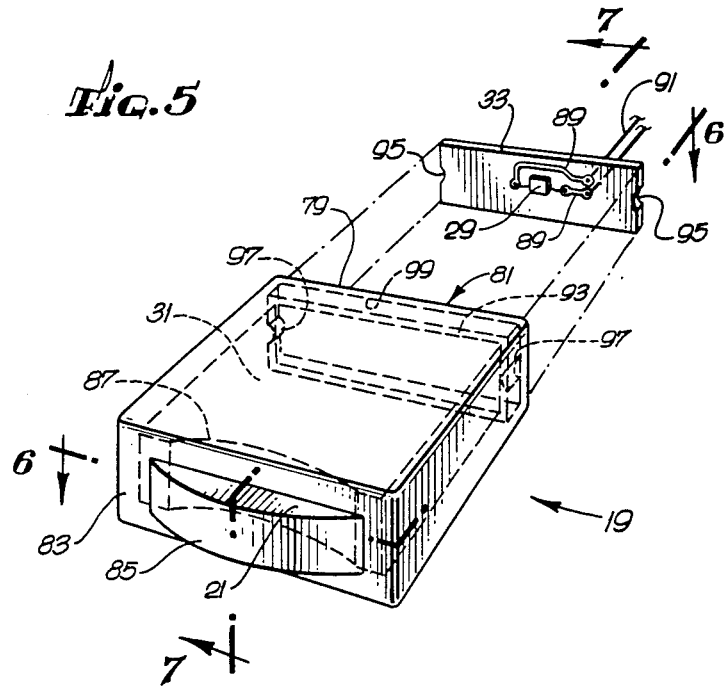
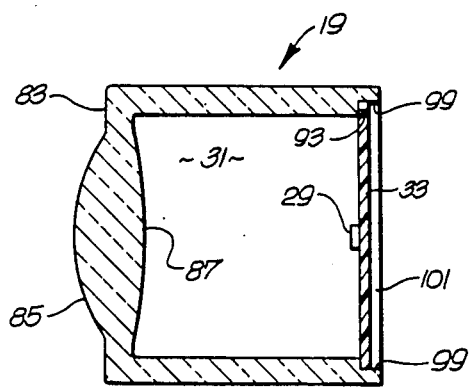
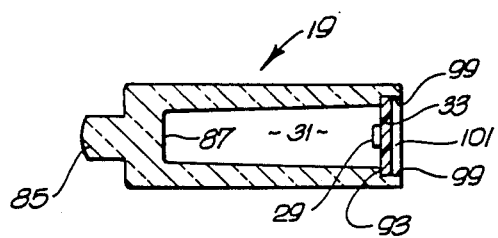

OPTICAL FLOW SENSOR

BACKGROUND OF THE INVENTION

1. Field of the Invention

The present invention relates generally to apparatus for sensing the flow of a fluid, and more particularly to apparatus for detecting and measuring, by optical means, the flow of a fluid that flows slowly enough for individual drops to be detected.

2. The Prior Art

A fluid flow sensor that can detect and measure the flow of individual drops of a fluid has many applications. A primary application for such a sensor is measuring the flow of fluid through a drip chamber assembly in an intravenous ("IV") fluid infusion system. Such an IV fluid infusion system generally includes a bottle containing a fluid to be administered; a drip chamber assembly; a tube connecting the bottle to an inlet at the top of the drip chamber; a valve, associated with the tube, to control the rate of flow of the fluid; a second tube connected to an outlet at the bottom of the drip chamber; and injecting means such as a hypodermic needle or catheter connected to the second tube through which the fluid passes into the patient.

A drip chamber assembly is usually cylindrical in shape and has transparent walls enclosing a drip chamber. The fluid enters the assembly through a drop former at the top of the chamber and falls, one drop at a time, through the chamber. The flow of the fluid through the chamber can be monitored by visually observing the falling drops, but various kinds of flow sensors have been developed to detect the fall of these drops automatically and thereby free the human observer for other tasks.

Examples of fluid flow sensors that can monitor the flow of fluid through a drip chamber assembly are disclosed in U.S. Pat. No. 3,596,515, issued to Cramer on Aug. 3, 1971, and U.S. Pat. No. 4,397,648, issued to Knute on Aug. 9, 1983, both assigned to the assignee of the present application. A few sensor of the kind disclosed in these patents generally employs an optical energy emitter on one side of the drip chamber asembly and an optical energy detector on the other side. The energy emitter usually emits optical energy in the infrared or visible light spectra (wavelength between about 300 nanometers and 2 microns). This optical energy passes through the transparent walls of the drip chamber assembly and then strikes the detector. As each individual drop falls through the chamber, it interrupts the flow of optical energy, causing the detector to produce a corresponding output signal. This output signal is then applied to a monitoring device for further processing. The monitoring device typically either sounds an alarm if the fluid stops flowing or monitors the rate of flow of the fluid.

Existing flow sensors such as those disclosed in the cited patents have certain shortcomings. One of these is the need accurately to align the energy emitter and detector during manufacture, a procedure that adds significantly to the overall cost of making flow sensors. It would be possible to manufacture flow sensors more economically if this step could be simplified or eliminated.

Also, the detector must be shielded so that it will not be affected by ambient optical energy, and all of the parts in the optical path must be kept clean to prevent a reduction in sensitivity that can result from dirt or moisture interfering with the passage of optical energy. A sensor that is less sensitive to ambient energy than existing sensors, and that is easier to clean, would be more reliable and easier to use in the field than existing sensors.

In addition, the transparent walls of the drip chamber assembly refract the optical energy as it passes through. This refraction renders the detector unable to detect drops of fluid that do not pass near the center of the chamber as they fall. If the chamber is kept in a nearly vertical orientation, the detector will be able to detect the drops without difficulty because they will all fall through the center of the chamber, but if the chamber is tilted more than about 15 degrees away from a vertical orientation, the drops will tend not to fall through the center of the chamber and the detector will be unable to detect them. A flow sensor that could function properly when used with a tilted drip chamber as well as with a chamber that is constrained in a vertical orientation would be more versatile, would be easier to use, and would be less likely to give a false "not flowing" alarm than existing flow sensors.

The use of IV systems as essential elements of modern medical care is continuing to expand, and with this expanding use has come a growing demand for IV systems that can function with a minimum of human monitoring. This demand has in turn led to a need for a fluid flow sensor that can be more economically manufactured than existing sensors, that is relatively unaffected by ambient optical energy or by dust and moisture in the environment, and that can detect the flow of fluid through a drip chamber even if the chamber is tilted far from its vertical axis.

One suggested approach to this problem is to employ a non-standard drip chamber assembly having walls formed in the shape of special lenses that can focus rays of light through the drip chamber and onto a photosensitive chip of material located adjacent thereto. However, such drip chamber assemblies are relatively costly to manufacture, and a fluid flow sensor adapted for use with them cannot be used with conventional cylindrical drip chamber assemblies. Unlike a conventional cylindrical assembly, the lens-shaped walls of such a non-standard drip chamber are rigid, making it more difficult to prime the system. In addition, this approach does not address the problems caused by noise, dirt and moisture in the environment.

It will be apparent from the foregoing that there is a need for an optical fluid flow sensor that can be used with conventional cylindrically-shaped drip chamber assemblies, that can be manufactured more economically than can existing sensors, that is relatively insensitive to ambient energy and that is easy to keep clean in the field, and that can detect the flow of fluid even if the drip chamber assembly is tilted far from a vertical orientation. The present invention satisfies this need.

SUMMARY OF THE INVENTION

The present invention is characterized by a chip of optical energy-emitting material positioned generally at the focal point of a first refracting lens and a chip of optical energy-detecting material positioned generally at the focal point of a second refracting lens. The first lens focuses the emitted optical energy into a beam of optical rays that are directed towards the second lens, and the second lens focuses the received beam onto the detector. There is a space between the two lenses for receiving a drip chamber assembly. The lenses are specially formed to refract the optical energy so as to compensate for the refraction caused by the walls of the drip chamber assembly, and the detector is therefore responsive to drops falling through the chamber at any point between the vertical axis and the chamber walls.

The chip of optical energy-emitting material, unlike a standard light-emitting diode ("LED"), does not have a built-in lens. Instead, this chip is sealed inside a hollow block of transparent material that has a refracting lens formed in one of its sides. Likewise, the detector chip has no built-in lens but is sealed inside a second hollow transparent block that also has a refracting lens formed in one of its sides. The two lens blocks are installed on a supporting base with their lenses facing each other and separated by a space large enough to accommodate a drip chamber assembly. The lens blocks are self aligning during manufacture of the sensor, and manufacturing cost is accordingly reduced.

Sealing the emitter and detector chips into their respective lens blocks keeps them permanently free of dust and moisture. The only surfaces that must be cleaned are the exterior lens surfaces of the two blocks, and these two surfaces are readily accessible and can be washed whenever necessary. Also, the detector lens block is easily shielded to block out unwanted optical energy.

It will be appreciated from the foregoing that the present invention represents a significant advance in optical fluid flow measuring apparatus. Specifically, this invention provides a fluid flow sensor that is economical to manufacture because the lens blocks are selfaligning, that is easy to shield against ambient optical energy, that is easy to keep free of dust and moisture, and that responds to drops that fall off-center as well as to those that fall along the vertical axis of the drip chamber.

Other aspects and advantages of the present invention will become apparent from the following more detailed description taken in conjunction with the accompanying drawings.

BRIEF DESCRIPTION OF THE DRAWINGS

FIG. 5 is an enlarged exploded perspective view of a lens block;

FIG. 6 is a horizontal section view taken generally along the line 6—6 of FIG. 5; and FIG. 7 is a vertical section view taken generally along the line 7—7 of FIG. 5.

DESCRIPTION OF THE PREFERRED EMBODIMENT

Existing optical flow sensors are characterized by relatively high manufacturing cost, sensitivity to ambient optical energy, dirt, and moisture, and the inability to respond to drops falling far from the vertical axis of a drip chamber assembly. The present invention employs unique lens block assemblies to overcome these limitations and in particular to provide a flow sensor that is responsive to drops falling near the walls of the drip chamber as well as to those falling near its vertical axis.

Figure 1:
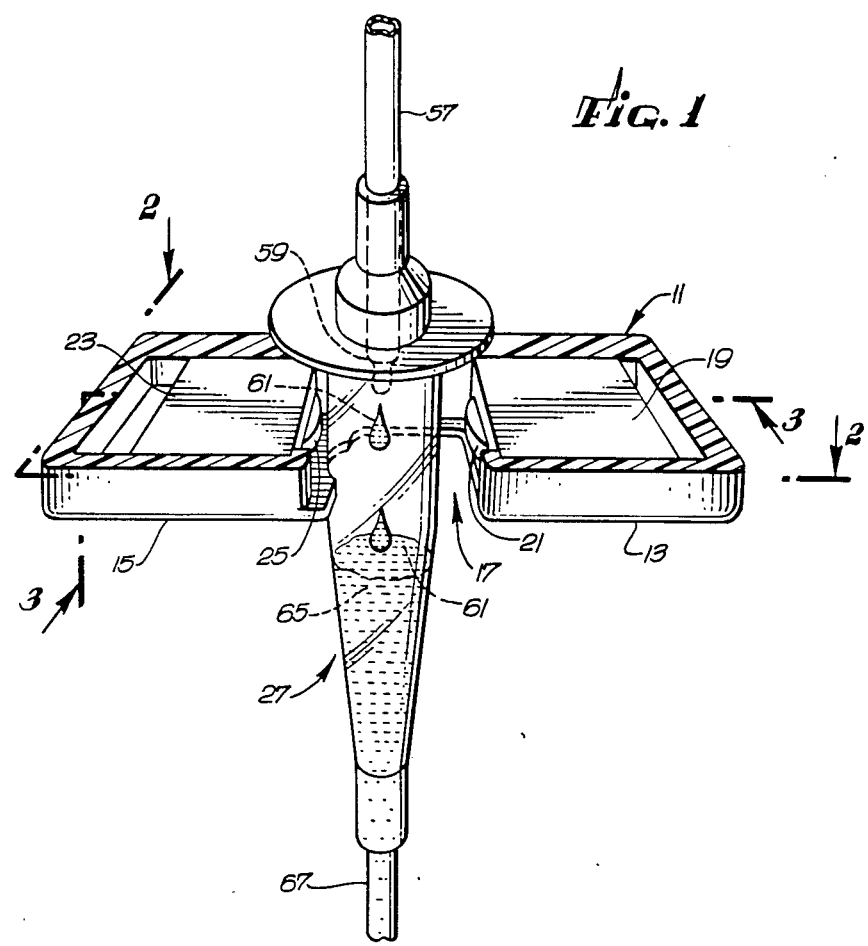
FIG. 1 is a perspective view of an improved optical flow sensor embodying the novel features of the invention and shown in operative relation with a drip chamber assembly of an intravenous fluid infusion system.

An improved fluid flow sensor embodying the invention, with a drip chamber assembly in position, is shown in FIG. 1. The sensor comprises a supporting base 11 having a first arm 13 and a second arm 15 with a space 17 between the two arms. An emitter block 19 having a lens 21 is mounted on arm 13, with lens 21 oriented towards space 17, and an energy detector block 23 having a lens 25 is mounted on arm 15, with lens 25 oriented to face lens 21 across space 17. A drip chamber assembly 27 is positioned within space 17 between emitter lens 21 and detector lens 25.

Figure 2:
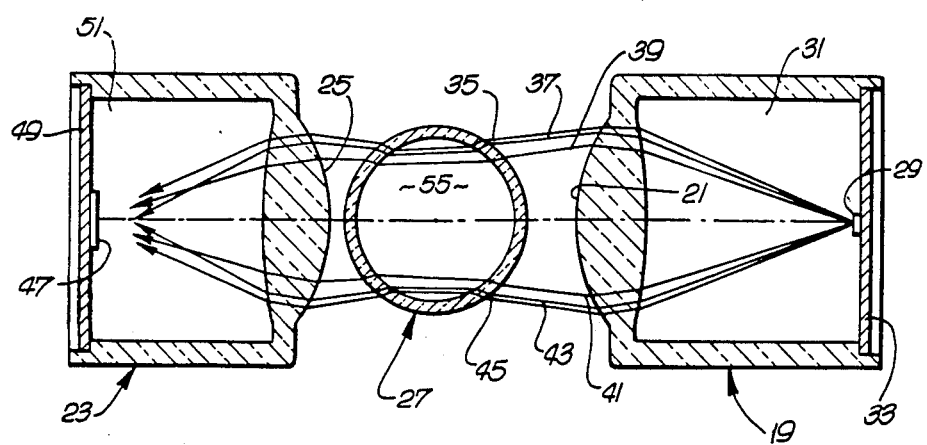
FIG. 2 is a somewhat schematic horizontal section view taken generally along the line 2—2 of FIG. 1, showing emitter and detector blocks with a drip chamber assembly therebetween.
Figure 3:
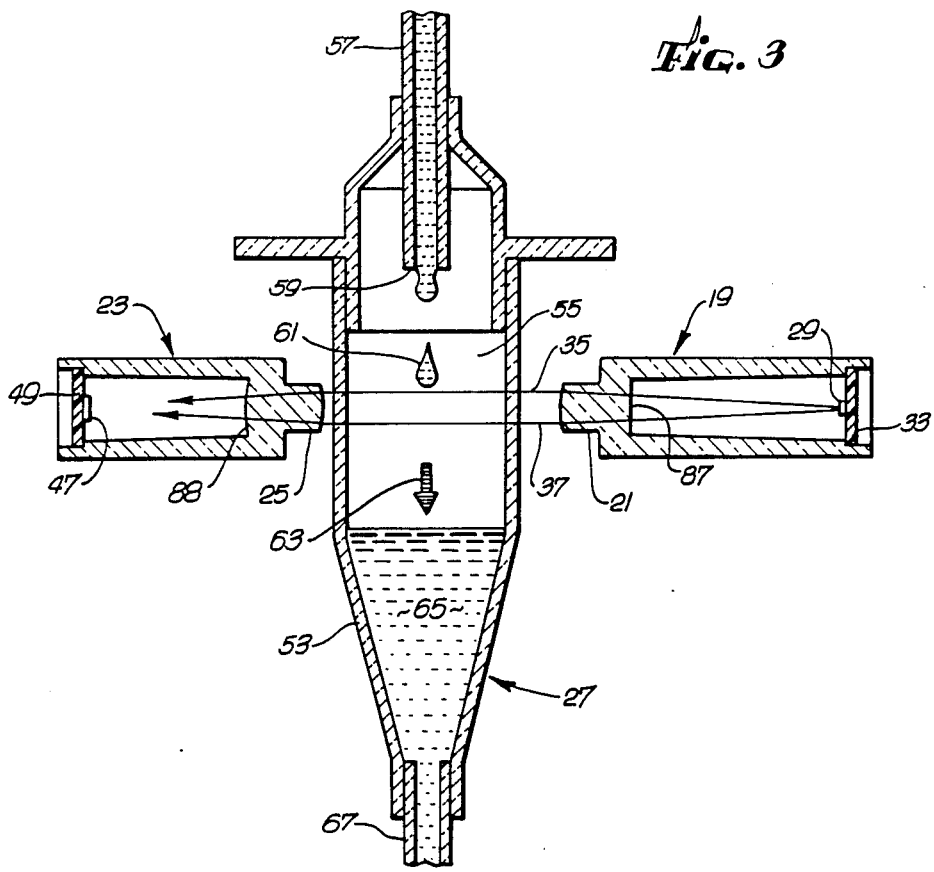
FIG. 3 is a somewhat schematic vertical section view taken generally along the line 3—3 of FIG. 1.

Energy emitting chip 29 is installed within cavity 31 in block 19, as shown in FIG. 2 and FIG. 3 (supporting base 11 has been omitted from FIG. 2 and FIG. 3 for clarity). Chip 29 is mounted on printed circuit board 33 within block 19 and is located generally at the focal point of lens 21. A beam of optical energy having rays 35, 37, 39, 41, 43 and 45 is emitted from chip 29 and refracted by lens 21, and this beam then passes through drip chamber assembly 27 to lens 25. Lens 25 focuses the beam onto detector chip 47. Detector chip 47 is mounted on circuit board 49 within cavity 51 of block 23. Detector chip 47 is located generally at the focal point of lens 25.

Drip chamber assembly 27 is generally cylindrical in shape, as shown in FIGS. 1 and 3. Assembly 27 has transparent cylindrical wall 53 defining drip chamber 55. An inlet tube 57 leads into the top of chamber 55. Drop former 59 comprises an end of tube 57, and as fluid flows through tube 57, individual drops 61 of fluid form at drop former 59 and fall through chamber 55 as indicated by arrow 63 into a reservoir of fluid 65 in the lower portion of chamber 55. Fluid flows from reservoir 65 out of chamber 55 through outlet tube 67. As individual drops 61 of fluid fall through chamber 55, they intersect some of optical energy rays 35, 37, 39, 41, 43 and 45, causing a fluctuation in the intensity of the energy beam that strikes detector chip 47.

Detector chip 47 generates an electrical output signal that changes in response to fluctuations in the intensity of the optical energy striking the chip. As each drop 61 of fluid falls through drip chamber 55 and causes the intensity of the optical energy to fluctuate, the output signal from chip 47 changes accordingly. Each change in the output signal is therefore indicative of the passage of one drop of fluid through chamber 55. Optical energy from emitter 29 passes through virtually the entire width of chamber 55, and therefore drops that pass near the edges of chamber 55, as well as drops that pass through the center of chamber 55, are detected.

The output signal is applied to electronic monitoring apparatus (not shown). Said apparatus may be configured to determine the rate of flow of the fluid by measuring the time interval between the fall of successive drops, or it may be configured to activate an alert signal if no drops fall during a predetermined interval of time.

Suitable retaining means (not shown) may be provided to retain drip chamber assembly 27 in fixed position in space 17.

The sensitivity of the flow sensor can be improved by increasing the ratio between the width of drops 61 of fluid and the width of the energy beam that strikes detector chip 47. This is because the magnitude of a change in the output signal from chip 47 caused by a drop of fluid intersecting the optical energy beam is proportional to the magnitude of the fluctuation in the intensity of the energy beam striking chip 47, and as the percentage of the total energy beam that is intersected by a drop of fluid increases, the magnitude of the fluctuation in beam intensity caused by a falling drop also increases. Since the size of the drops is governed by other considerations and cannot be changed for purposes of improving the sensitivity of the flow sensor, the only way to increase the ratio between the drop width and the beam width is to reduce the beam width. The width of the beam can be reduced by installing an aperture assembly in detector block 23, as illustrated in FIG. 4.

Figure 4:
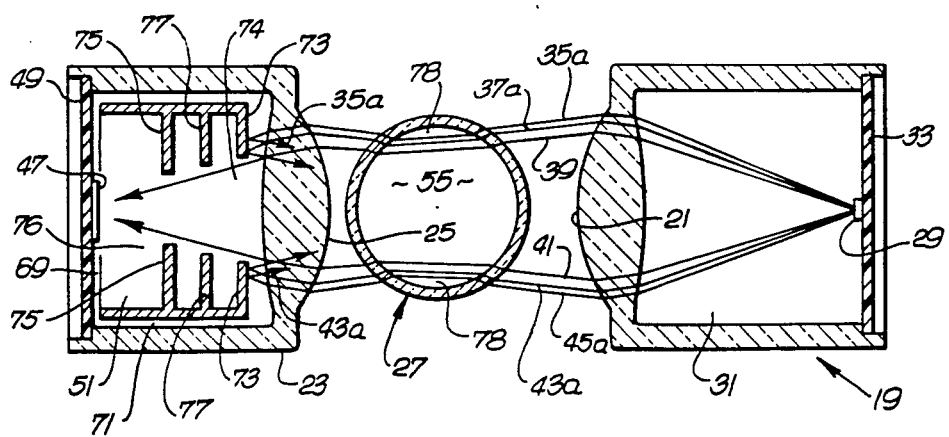
FIG. 4 is a section view similar to the view shown in FIG. 2, except that an aperture assembly has been added within the detector block.

The embodiment of the invention shown in FIG. 4 is similar to that shown in FIG. 2. For convenience, components in FIG. 4 that are similar to components in FIG. 2 are assigned the same reference numerals; analogous but changed components are assigned the same reference numerals accompanied by the letter "A"; and different components are assigned different reference numerals.

Aperture assembly 69, having opaque side walls 71, opaque front walls 73, and an opaque top and bottom (not shown), is positioned within the hollow area 51 in detector block 23 with front walls 73 adjacent the interior surface of lens 25. The top, the bottom, and side walls 71 of assembly 69 shield detector chip 47 from optical energy that might enter block 23 through any of its surfaces other than the surface having lens 25 formed therein. Front walls 73 extend from side walls 71 part way across lens 25 defining an aperture 74. Aperture 74 admits optical energy, represented by rays 39 and 41, that does not pass through extreme left and right side areas 78 of drip chamber 55, but excludes optical energy, represented by rays 35A, 37A, 43A, and 45A, that passes through side areas 78 of chamber 55. Only energy admitted through aperture 74 strikes detector chip 47; front walls 73 block other energy and scatter it away.

The width of the energy beam that strikes detector chip 47 can be narrowed by making aperture 74 narrower and widened by making aperture 74 wider. As the beam of energy that is admitted by aperture 74 becomes narrower, the ratio of the width of a drop to the total beam width becomes greater annd chip 47 therefore becomes more sensitive to drops falling through chamber 55. However, drops that fall through side areas 78 of chamber 55 are not detected because the portion of the beam of energy that such drops intersect, represented by rays 35A, 37A, 43A and 45A, never reaches chip 47 but instead is scattered away by walls 73. Therefore, as aperture 74 becomes narrower, side areas 78, within which falling drops cannot be detected, become wider. The tradeoff, then, is that as aperture 74 becomes narrower, chip 47 becomes more sensitive to falling drops but the portion of drip chamber 55 within which falling drops can be detected becomes narrower.

If drip chamber assembly 27 is constrained in a perfectly vertical position, drops 61 will fall only through the center of drip chamber 55 and will be detected even if a very narrow aperture 74 is used. But as assembly 27 is tilted farther away from a vertical orientation, drops 61 will tend to fall closer and closer to the edges of chamber 55, and if assembly 27 is tilted far enough, the drops will fall through one of the side areas 78 and detector chip 47 will fail to respond to them.

In other words, as aperture 74 becomes narrower, chip 47 becomes more sensitive and the maximum tilt angle of drip chamber 55 at which drops can be reliably sensed becomes smaller. A useful compromise is to make aperture 74 narrow enough that each of side areas 78 is as wide as one drop. This compromise gives good sensitivity and enables the sensor reliably to detect the passage of drops through a drip chamber assembly that is tilted not more than 26 degrees from the vertical.

Optionally, opaque baffles 75 can be installed within aperture assembly 69 between front walls 73 and detector chip 47. Baffles 75 form a surface parallel to front walls 73 and defining a second aperture 76 that is narrower than aperture 74. Baffles 75 reduce the effects on chip 47 of ambient optical energy by scattering much of such energy away. Still further immunity to such ambient energy can be achieved by adding a second set of baffles 77, and even more such baffles could also be added, as will be apparent to those skilled in the art.

Turning now to a more detailed description of energy emitter block 19, said block is formed from a hollow block of transparent material as shown in FIG. 5. Rear side 79 of block 19 has an opening 81 into cavity 31 in the interior of block 19. Lens 21 is formed in front side 83 of block 19, said lens having a convex exterior surface 85 and a convex interior surface 87. The shapes of exterior and interior surfaces 85 and 87 of lens 21 are formed according to the refractive effects of the walls of drip chamber assembly 27; in the preferred embodiment described and illustrated herein, exterior lens surface 85 is convex both in its horizontal cross-section and in its vertical cross-section as shown in FIGS. 6 and 7, respectively, and interior lens surface 87 is convex only in its horizontal cross-section.

Energy emitting chip 29 is installed on circuit board 33 and is connected to printed wiring conductors 89. Wires 91 are connected to conductors 89 for making connections between chip 29 and an external circuit (not shown).

A shoulder 93 is formed along the perimeter of opening 81, said shoulder being recessed a short distance into cavity 31, said distance being slightly greater than the thickness of circuit board 33. Circuit board 33 has the same width and length as does opening 81, and the circuit board is positioned in said opening against shoulder 93. Notches 95 in circuit board 33 engage alignment keys 97 extending rearwardly from shoulder 93, retaining circuit board 33 in fixed orientation with respect to block 19. Lens 21 is formed such that chip 27 is generally at the focal point of lens 21 when circuit board 33 is positioned against shoulder 93 with notches 95 engaging alignment keys 97.

When circuit board 33 is in position against shoulder 93 within opening 81, the circuit board closes off the only access between cavity 31 and the outside world, and the circuit board in combination with the interior edges 99 of opening 81 defines a recessed area 101. Recessed area 101 may be filled with potting material (not shown), thereby sealing block 19 and protecting cavity 31 from dust, moisture, or other contaminants that may be present in the atmosphere. Ideally, assembly and potting of circuit board 33 into block 19 will be performed in a dry, inert atmosphere such as nitrogen. The assembled block can then be washed or subjected to dusty or other harsh atmospheres without harming chip 29 or causing condensation on interior lens surface 87.

The structure of detector block 23 is generally similar to the structure of emitter block 19, except that the chip 47 installed within the former is an optical energy detecting device whereas the chip 29 installed within the latter is an optical energy emitter. Also, the two lenses have slightly different focal lengths. In addition, in the preferred embodiment described and illustrated herein, interior surface 88 of detector lens 25 is convex both in its horizontal cross-section and in its vertical crosssection, as shown in FIG. 3, whereas interior lens surface 87 of emitter lens 21 is convex only its horizontal crossection. It will be understood, therefore, that the preceding description of the structure of emitter block 19 also pertains to the structure of detector block 23 except as noted in this paragraph.

A fluid flow sensor as described can be used with any drip chamber assembly having transparent walls and being of a physical size that will fit within the space 17 between emitter block 19 and detector block 23.

Immunity to ambient optical energy is good because lens 25 tends not to focus such light onto detector chip 47. This immunity can be improved by using an aperture assembly 69, and if desired may be still further improved by employing an energy emitter that emits infrared energy and a filter or other means (not illustrated) to render detector chip 47 insensitive to any optical energy that is not within the infrared spectrum.

Assembly of a fluid flow sensor embodying the present invention is simpler than assembly of a prior art sensor. Instead of having to align physically small energy emitters and energy detectors with respect to a sensor base and with respect to each other, an assembler need only mount the two lens blocks so that their lenses face one another. In addition, a fluid flow sensor embodying the present invention needs no additional shielding from ambient energy and, because the energy detector and emitter chips are sealed, the only optical parts that must be kept free of dust and moisture are the exterior lens surfaces of the two blocks. The present invention also provides a sensor responsive to drops falling far from the vertical axis of the drip chamber, and therefore works equally well with drip chamber assemblies that are tilted as much as 26 degrees as with vertically-oriented assemblies.

Of course, many variations and modifications of the present invention are possible in light of the above teachings. For example, the radii of curvature of the various lens surfaces may be changed to correct for the different refractive effects of various different drip chamber assemblies. Moreover, although the invention has been disclosed in the specific context of an IV fluid flow monitor, it has application to any product in which it is desirable to measure fluid flow or sense the lack of such flow by optical means. It is therefore to be understood that, within the scope of the appended claims, the invention may be practiced otherwise than as specifically described.

We claim:

1. A fluid flow sensor comprising:
   a supporting base having a first arm and a second arm generally parallel to the first arm and separated therefrom to define a space;
   a drip chamber assembly having transparent walls defining a drip chamber, said walls having a refractive effect upon energy entering and exiting the chamber therethrough;
   means, located within the drip chamber, for forming said fluid into drops, operative to cause said drops to fall through the chamber;
   retaining means for retaining said drip chamber assembly in a predefined position within the space;
   an energy emitter mounted on the first arm;
   first energy refracting means, mounted in fixed relationship to the energy emitter, oriented to receive energy emitted by said emitter and operative to refract said energy toward said drip chamber assembly in a pattern that has been predetermined with reference to the refractive effects of the walls of said drip chamber assembly to cause said energy to pass through substantially the entire width of said drip chamber;
   an energy detector mounted on the second arm; and
   second energy refracting means, mounted in fixed relationship to the energy detector, oriented to receive said pattern of energy that has been refracted by the first refracting means and further refracted upon passing through the walls of said drip chamber assembly, and operative to still further refract said energy onto the energy detector;
   at least one of said energy refracting means comprising a hollow block of transparent material having a refracting lens formed in a lens side thereof and oriented with said lens generally facing the predefined position.

2. a fluid flow sensor according to claim 1 wherein the energy emitted by the emitter is in the infrared spectrum and comprising in addition filtering means positioned between the energy emitter and the energy detector, operative to attenuate energy that is not in the infrared spectrum.

3. A sensor according to claim 1, comprising in addition an aperture assembly having an opaque front wall defining therein an aperture opening and disposed between the drip chamber assembly and the energy detector to prevent a predetermined portion of the energy passing through the walls of the drip chamber assembly from reaching the energy detector.

4. A sensor according to claim 3, comprising in addition an opaque baffle within the aperture assembly, the baffle having an opaque wall generally parallel to the front wall and defining therein a baffle aperture opening.

5. A fluid flow sensor for monitoring the flow of a fluid through a drip chamber assembly of the kind having transparent walls defining a chamber and means for forming said fluid into drops that fall through the chamber, said walls having a refractive effect upon energy entering and exiting the chamber therethrough, comprising:
   a supporting base having a first arm and a second arm generally parallel to the first arm and separated therefrom to define a space;
   retaining means affixed to said base for retaining the drip chamber assembly in a predefined position within the space;
   a first hollow block of transparent material mounted on the first arm, said block having a lens side, said lens side being oriented generally facing said predefined position;
   an energy emitter, mounted within the hollow area of the first block, oriented to emit energy generally toward the lens side of said block;
   a first refracting lens formed in the lens side of the first block, operative to refract energy emitted by the energy emitter toward said predefined position in a pattern that has been predetermined with reference to the refractive effects of the walls of the drip chamber assem- bly;

a second hollow block of transparent material mounted on the second arm, said block having a lens side, said lens side being oriented generally facing said predefined position;

an energy detector, mounted within the hollow area of the second block, oriented to detect energy coming generally from the lens side of said block; and a second refracting lens formed in the lens side of the second block, operative to receive said pattern of energy that has been refracted by the first refracting means and further refracted upon passing through the walls of said drip chamber assembly, and to still further refract said energy onto the energy detector.

6. A fluid flow sensor according to claim 5 wherein the energy emitted by the emitter is in the infrared spectrum and comprising in asddition filtering means positioned between the emitter and the energy detector operative to attenuate energy that is not in the infrared spectrum.

7. A fluid flow sensor according to claim 5, comprising in addition a first printed circuit board and a second printed circuit board, the energy emitter being mounted on said first board and said first board in turn being mounted in the first hollow block, the energy detector being mounted on said second board and said second board in turn being mounted in the second hollow block.

8. A fluid flow sensor according to claim 5, comprising in addition an aperture assembly having a plurality of opaque side walls and an opaque front wall, said front wall having an aperture opening, said assembly being installed within said second lens block with the aperture opening generally adjacent the lens surface of the block.

9. A fluid flow sensor according to claim 8, comprising in addition an opaque baffle within the aperture assembly, the baffle comprising an opaque wall generally parallel to the front wall and having therein a baffle aperture opening.

10. In a fluid flow sensor for monitoring the flow of a fluid in a drip chamber assembly of the kind having transparent walls defining a chamber and means for forming said fluid into drops that fall through the chamber, said walls having a refractive effect upon energy entering and exiting the chamber therethrough, the sensor including an energy emitter positioned on one side of the drip chamber, an energy detector on the other side thereof, supporting means for holding said emitter and said detector in fixed position with respect to each other, and means for retaining the drip chamber assembly in a predefined position between said emitter and said detector, an improvement comprising:

first energy refracting means, mounted in fixed relationship to the energy emitter, oriented to receive energy emitted by said emitter and operative to refract said energy toward said predefined position in a pattern that has been predetermined with reference to the refractive effects of the walls of said drip chamber assembly to cause said energy to pass through substantially the entire width of said drip chamber; and second energy refracting means, mounted in fixed relationship to the energy detector, oriented to receive said pattern of energy has been refracted by the first refracting means and further refracted upon passing through the walls of said drip chamber assembly, and operative to still further refract said energy onto the energy detector;

at least one of said energy refracting means comprising a hollow block of transparent material having a refracting lens formed in a lens side thereof and oriented with the lens generally facing the predefined position.

11. An improvement according to claim 10 wherein the energy emitted by the emitter is in the infrared spectrum and comprising in addition filtering means positioned between the emitter and the energy detector for attenuating energy that is not in the infrared spectrum.

12. An improvement according to claim 10, comprising in addition an aperture assembly having an opaque front wall defining therein an aperture opening and disposed between the drip chamber assembly and the energy detector to prevent a predetermined portion of the energy passing through the walls of the drip chamber assembly from reaching the energy detector.

13. An improvement according to claim 12, comprising in addition an opaque baffle witnin the aperture assembly, the baffle having an opaque wall generally parallel to the front wall and defining therein a baffle aperture opening.

14. In a fluid flow sensor for monitoring the flow of a fluid in a drip chamber assembly of the kind having transparent walls defining a chamber and means for forming said fluid into drops that fall through the chamber, said walls having a refractive effect upon energy entering and exiting the chamber therethrough, the sensor including an energy emitter positioned on one side of the drip chamber, an energy detector on the other side thereof, supporting means for holding said emitter and said detector in fixed position with respect to each other, and means for retaining the drip chamber assembly in a predetermined position between said emitter and said detector, an improvement comprising:

first energy refracting means, mounted in fixed relationship to the energy emitter, oriented to receive energy emitted by said emitter and operative to refract said energy toward said predefined position in a pattern that has been predetermined with reference to the refractive effects of the walls of said drip chamber assembly, said first energy refracting means including a first hollow block of transparent material having a first refracting lens formed in a lens side thereof, said energy emitter being mounted within the hollow interior of said first block, positioned generally at a focal point of said first lens; and second energy refracting means, mounted in fixed relationship to the energy detector, oriented to receive said pattern of energy that has been refracted by the first refracting means and further refracted upon passing through the walls of said drip chamber assembly, and operative to still further refract said energy onto the energy detector, said second energy refracting means including a second hollow block of transparent material having a second refracting lens formed in a lens side thereof, said energy detector being mounted within the hollow interior of said block, positioned generally at a focal point of said lens.

15. An improvement according to claim 14, comprising in addition an aperture assembly having a plurality of opaque side walls and an opaque front wall, said front wall having an aperture opening, said assembly being installed within said second lens block with the aperture opening generally adjacent the lens surface of the block.

16. An improvement according to claim 15, comprising in addition an opaque baffle within the aperture assembly, the baffle comprising an opaque wall generally parallel to the front wall and having therein a baffle aperture opening.

17. An improvement according to claim 14 wherein the energy emitted by the emitter is in the infrared spectrum and comprising in addition filtering means positioned between the emitter and the energy detector for attenuating energy that is not in the infrared spectrum.

18. A fluid flow sensor for monitoring the flow of a fluid in a drip chamber assembly of the kind having transparent walls defining a chamber and means for forming said fluid into drops that fall through the chamber, said walls having a refractive effect upon energy entering and exiting the chamber therethrough, the sensor comprising:
   an energy emitter;
   an energy detector in a fixed, spaced-apart relationship to the emitter and defining therebetween a space to receive said drip chamber;
   first energy refracting means in fixed relationship to the energy emitter, oriented to receive energy emitted by said emitter and operative to refract said energy toward said space in a pattern that has been predetermined with reference to the refractive effects of the walls of said drip chamber assembly to cause said energy to pass through substantially the entire width of said drip chamber; and
   second energy refracting means in fixed relationship to the energy detector, oriented to receive said pattern of energy that has been refracted by the first refracting means and further refracted upon passing through the walls of said drip chamber assembly, and operative to still further refract said energy onto the energy detector;
   at least one of aid energy refracting means comprising a hollow block of transparent material having a refracting lens formed in a lens side thereof and oriented with said lens generally facing said space.

19. A sensor according to claim 18 wherein the energy emitted by the emitter is in the infrared spectrum and comprising in addition filtering means positioned between the emitter and the energy detector for attenuating energy that is not in the infrared spectrum.

20. A sensor according to claim 18 and further comprising an aperture assembly having an opaque front wall defining therein an aperture opening and disposed between the space and the energy detector to prevent a predetermined portion of the energy passing through the walls of the drip chamber assembly from reaching the energy detector.

21. A sensor according to claim 20, comprising in addition an opaque baffle within the aperture assembly, the baffle having an opaque wall generally parallel to the front wall and defining therein a baffle aperture opening.

* * * * *